DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED FEBRUARY 3, 1976

943 O.G. 74

T943,002

PROCESS FOR THE OXIDATION OF OLEFINICALLY UNSATURATED COMPOUNDS TO CARBONYL COMPOUNDS

Hugh J. Hagemeyer, Jr., and Frank C. Canter, both of P.O. Box 2068, Longview, Tex. 75603, and Ronald A. De Jean, % Alpart, Spun Tree, Jamaica, British West Indies

Continuation of abandoned application Ser. No. 858,186, Sept. 15, 1969. This application June 26, 1974, Ser. No. 483,473

Int. Cl. C07c *47/06*

U.S. Cl. 260—604 AC

No Drawing. 21 Pages of Specification

A process for the oxidation of olefinically unsaturated compounds to carbonyl compounds comprising contacting the olefinically unsaturated compounds with an aqueous oxidizing agent in the presence of a catalyst comprising an aqueous solution which includes a catalytically active palladium compound, cupric chloride, and sufficient insoluble cuprous chloride to provide a heterogeneous aqueous catalyst solution having an absolute emf value of about 260 to about 400 mv.